United States Patent [19] [11] 4,397,946
Imada et al. [45] Aug. 9, 1983

[54] PROCESS FOR PREPARING ANDROSTANE STEROIDS

[75] Inventors: Yukio Imada; Tetsu Osozawa, both of Machida; Yuki Morimoto, Yokohama; Masayuki Kinoshita, Ibaragi, all of Japan

[73] Assignee: Mitsubishi Chemical Industries Limited, Tokyo, Japan

[21] Appl. No.: 267,242

[22] Filed: May 26, 1981

[30] Foreign Application Priority Data

Jun. 17, 1980 [JP] Japan .................................. 55-81943

[51] Int. Cl.³ .......................... C12P 33/16; C12N 1/38
[52] U.S. Cl. ..................................... 435/55; 435/244; 435/863
[58] Field of Search ........................................... 435/55

[56] References Cited

U.S. PATENT DOCUMENTS 3,388,042 6/1968 Arima et al. ........................... 435/55
4,101,378 7/1978 Nishikawa et al. ................... 435/55
4,179,336 12/1979 Weber et al. ......................... 435/55

Primary Examiner—Alvin E. Tanenholtz
Attorney, Agent, or Firm—Oblon, Fisher, Spivak, McClelland & Maier

[57] ABSTRACT

Androstane steroids are produced by microbiological conversion of a sterol substrate with a microorganism belonging to the genus Mycobacterium wherein the medium used contains at least 0.1% by weight of egg yoke as a dry weight.

11 Claims, No Drawings

PROCESS FOR PREPARING ANDROSTANE STEROIDS

BACKGROUND OF THE INVENTION

1. Field of the Invention

This invention relates to a process for producing androstane steroids. More particularly it relates to an improvement in the culture medium used in the fermentative production of androstane steroids.

2. Description of the Prior Art

It is well known in the art that an androstane steroid can be produced by microbiological conversion of a sterol with a microorganism belonging to the genus Mycobacterium (hereinafter abbreviated as "M."). However, this method involves some disadvantages in that the yield of the desired steroid is not yet satisfactory with the rate of production being low.

It is also known that in the steroid fermentation wherein progesterone is hydroxylated at the 11α-position with the aid of *Rhizopus nigricans* one of fungi, the substrate (i.e., progesterone) can be fed at a higher concentration by adding it as a mixture with raw egg yolk in the course of incubation, as compared with the cases where progesterone is added as a solution in acetone without use of raw egg yolk (Japanese Patent Publication No. 9765/1957).

SUMMARY OF THE INVENTION

This invention resides in a process for producing an androstane steroid by microbiological conversion of a sterol substrate with a microorganism belonging to the genus M. wherein the medium used contains at least 0.1% by weight of egg yolk as a dry weight.

DETAILED DESCRIPTION OF THE PREFERRED EMBODIMENTS

The androstane steroids that can be produced by the process of this invention include androst-4-ene-3,17-dione (hereinafter abbreviated as "4AD"), androsta-1,4-diene-3,17-dione ("ADD"), 9α-hydroxyandrost-4-ene-3,17-dione ("9α-OH-4AD"), dehydroepiandrosterone ("DHA"), dehydrotestosterone ("DHT"), testosterone ("TSN") and any other androstane steroid which is known in the prior art to be producible by microbiological conversion of a sterol substrate with a microorganism belonging to M. Of these androstane steroids, 4AD, ADD and 9α-OH-4AD are of particular importance as intermediates for the synthesis of various steroids.

The microorganism which can be used in the process of this invention may be any microorganism belonging to the genus M. and capable of producing the desired androstane steroid. Preferably the microorganism is a mutant which is lacking in or weak in the enzymes degrading the androstane steroid.

Examples of such mutant and the main androstane steroid products produced therewith are summarized in Table 1.

TABLE 1

| Androstane steroid | Microorganism |
|---|---|
| ADD | M. *parafortuitum* complex MCI-0801 |
| | M. *parafortuitum* complex MCI-0802 |
| | M. *vaccae* MCI-1102 |
| | M. *vaccae* MCI-1103 |
| | M. *vaccae* MCI-1115 |
| | M. *diernhoferi* MCI-1298 |
| | M. *diernoferi* MCI-1299 |
| 4AD | M. sp. NRRL B-3683 |
| | M. *parafortuitum* complex MCI-0807 |
| 9α-OH—4AD | M. sp. NRRL B-3805 |
| | M. *vaccae* MCI-1104 |
| | M. *vaccae* MCI-1117 |
| | M. *parafortuitum* MCI-1297 |
| | M. *fortuitum* NRRL B-8119 |

The sterol used in the present invention as a substrate includes various sterols, their C-3 ester or ether derivatives and the intermediates formed in the oxidation thereof.

Sterols possess a hydroxy group at C-3, normally a double bond at C-5, a side chain of 8 to 10 carbon atoms at C-17, and in some cases, a double bond at C-7, C-8, C-9 (11) or the like of the perhydrocyclopentanophenanthrene nucleus, although the cyclopentanophenanthrene nucleus may be saturated.

Examples of such sterols are cholesterol, stigmasterol, campesterol, β-sitosterol, ergosterol, brassicasterol, fucosterol, lanosterol, agnosterol, dihydrolanosterol, dihydroangosterol, and α-sitosterol. Especially preferred are cholesterol, campesterol and β-sitosterol.

C-3 ester derivatives of 3β-OH of sterols, and inorganic acids, e.g., sulfuric acid, or organic acids, e.g., fatty acids, can also be used as the starting material for the process of this invention. Examples of such C-3 ester derivatives are cholesteryl oleate, cholesteryl palmitate and cholesteryl sulfate.

Further, C-3 ether derivatives which are obtained, for example, by the addition of alkylene oxide to 3β-OH of sterols can be used as the starting material for the process of this invention. An example of such C-3 ether derivatives is polyoxyethylene cholesteryl ether.

It goes without saying that wool wax and lanolin each containing the above-described C-3 ester derivatives of the sterols; cholesterol-containing wool alcohol which is obtained by the hydrolysis of lanolin; and a C-3 ether derivative polyoxyethylene lanolin alcohol ether which is obtained by the reaction of wool alcohol with ethylene oxide can be used as the starting materials for the process of this invention.

Sterols-containing natural products and processed materials, such as waste oil obtained in purifying fish oil or cuttlefish oil by washing it with alkali, deodorized scum and sludge of vegetable oils, and tall oil can also be used as the starting materials for the process of this invention.

In addition, intermediates formed in the oxidation of sterols or their C-3 ester or ether derivatives can also be used as the starting material (substrates) for the process of this invention. The oxidation intermediates include 4-en-3-one or 1,4-dien-3-one derivatives of sterols or their C-3 ester or ether derivatives, for example, cholest-4-en-3-one, cholesta-4,22-dien-3-one, 3β-hydroxy-23,24-bisnorchol-5-en-22-oic acid, 3-oxo-23,24-bisnorchol-4-en-22-oic acid (hereinafter abbreviated as "4BN"), 3-oxopregna-4,17(20)-diene-20-carboxylic acid, methyl 3-oxopregna-4,17(20)-diene-20-carboxylate, cholic acid, lithocholic acid and the like.

It is an essential feature of this invention to use a medium containing at least 0.1% by weight of egg yolk as a dry weight.

The egg yolk may be in any of raw, dry and frozen form. It may be separated from the egg white. Alternatively, the whole egg in which the yolk is not separated from the egg white may be used, and in such cases the eggshell is usually removed. Of these forms of egg yolk, dry egg yolk is most conveniently used in a commercial operation.

The content of egg yolk in the medium must be at least 0.1% by weight as expressed in terms of dry egg yolk, and an amount of not more than 3% by weight egg yolk is generally satisfactory. If the amount of egg yolk is too small, any substantial effect of addition of egg yolk will not be produced. On the other hand, the use of an excessively large amount of egg yolk is not preferred since it tends to cause an inhibitory action to microorganisms. Usually the water content of raw egg yolks is 45 to 50% by weight.

In addition to the egg yolk, carbon sources, nitrogen sources and inorganic substances are added adequately to the culture medium used in the process of this invention.

Examples of the carbon sources are hydrocarbons such as n-paraffins, α-olefins and xylene; alcohols such as methanol, ethanol, glycerol and higher alcohols; organic acids such as succinic acid, acetic acid and higher fatty acids and their salts; glycerides, oils and fats such as soybean oil and cotton seed oil; and saccharides such as starch, maltose, sucrose, glucose and rhamnose.

Natural nutrient sources containing carbon sources, nitrogen sources and other nutrient substances may be incorporated in the culture medium. Examples of such natural nutrient sources are molasses including hightest molasses and xylose molasses; bagasse, corn cob, alfalfa, corn steep liquor, distillers' solubles, mieki (an aqueous solution of amino acids mixture prepared by the hydrolysis of soybean oil meal with HCl), fish meal, bran, meat extract, yeast, yeast extract, potato extract, malt extract, gluten, peptone, glutamates, asparagine, glycine, casein, casein hydrolysate, skimmed milk; vegetable oil meals such as soybean cake, rapeseed refuse, sesame meal, linseed meal and cotton seed meal; and oil seeds and oil fruits such as whole soybean, rapeseed, sesame, linseed and cotton seed.

Examples of the inorganic substances are nitrogen sources such as ammonium sulfate, ammonium chloride and the like; potassium and phosphorus sources such as dipotassium hydrogen phosphate; salts of iron, copper, magnesium, manganese, cobalt, zinc, calcium and the like; and ashes of natural products such as molasses. If necessary, other additives, e.g., vitamines may be added.

The composition of the culture medium depends on the microorganism which is used. Carbon sources, nitrogen sources, potassium, phosphorus and magnesium are critical as components in the culture medium.

A well-known anti-foaming agent, e.g., polyoxyalkylene glycol, may be incorporated in the culture medium, if necessary. However, it need not always be added.

A surfactant is preferably added to the medium since it is effective as an emulsifier for sterols. Preferred surfactants are nonionic or anionic ones, for example, polyoxyethylene sorbitan monostearate, sorbitan monopalmitate and polyethylene glycol monostearate.

The incubation temperature is usually 20° to 40° C. and most preferably in the range of about 25° to 35° C.

In general, the pH of the culture medium is adjusted to from 5 to 10, preferably from 6 to 9. Because the microorganism used in this invention belongs to the genus M., it can withstand even in a medium having a high pH value of about 10.

In general, the sterol that is the starting material for the process of this invention is sterilized along with the medium, although it may be added to the medium either all at once or in portions after the start of incubation. In the latter case, the sterol, after sterilization by dry heat or wet heat, is added as it is or in the form of a solution in a suitable solvent such as dimethylformamide or a finely dispersed suspension prepared by means of ultrasonic treatment. It is preferred to simultaneously add a surfactant because of the accelerated emulsification of the sterol substrate caused by such addition.

The incubation time is not critical. In general, the amount of the formed androstane steroid increases rapidly two days after the addition of the starting sterol. Then the amount of the formed androstane steroid increases gradually with the incubation time. However, the incubation time of exceeding 20 days is of little commercial value.

Upon completion of the incubation, the androstane steroid built up in the fermentation broth can be collected, isolated and purified in any conventional manner. For example, the broth can be extracted with several volumes of a water-immiscible organic solvent such as ethyl acetate. The extract is then distilled to remove the solvent, and the residual steroid mixture is subjected to column chromatography using porous resin, silica gel, alumina or the like as the adsorbent and petroleum ether, benzene, chloroform, ether, acetone, methanol, ethyl acetate or the like as the eluent to isolate the desired androstane steroid.

Usually, however, the incubation conditions and the extraction solvent can be so selected that the extract obtained by the solvent extraction of the fermentation broth predominantly comprises the desired androstane steroid. In such cases, pure crystals of the androstane steroid can be recovered, without chromatographic procedure, by distilling the extract to remove the solvent and then subjecting the residue to repeated recrystallization from acetone, hexane, cyclohexane or the like.

In accordance with the process of this invention, the effect on splitting off the side chain of a sterol is enhanced and the desired androstane steroid is produced at a significantly increased rate, as compared with the cases where an egg yolk-free medium is used. The yield of the androstane steroid based on the starting sterol is also increased. In addition, because of the increased rate of degradation of the starting sterol, it is possible to feed the sterol at a higher concentration as compared with the cases where no egg yolk is added. These favorable features, as a whole, result in a substantial increase in productivity of the androstane steroid and therefore the present invention is of great commercial value.

The egg yolk which is used in the process of this invention is very inexpensive compared with the product and this is another significant feature of this invention.

Having generally described this invention, a more complete understanding can be obtained by reference to certain examples which are provided herein for purposes of illustration only are not intended to be limiting in any manner.

In the examples, analysis of androstane steroids was made by gas chromatography and all the percentages are by weight.

EXAMPLE 1

A seed medium (pH 7.2) having the following composition is prepared:
- 1.0 percent of glucose
- 1.0 percent of meat extract
- 1.0 percent of peptone, and
- remainder-water.

To a 500 ml shaker flask is added 100 ml of the seed medium. The flask and its contents are sterilized by autoclaving for a period of 15 minutes at a temperature of 120° C. The medium is inoculated with a loopful of *m. parafortuitum* MCI-1297 and the inoculated medium is incubated for a period of 48 hours at a temperature of 30° C. on a reciprocal shaker having a 7-cm stroke at 120 strokes per minute.

To each of twenty (20) 500 ml shaker flasks which are divided into two groups each consisting of ten (10) flasks is added 50 ml of a main fermentation medium (pH 7.0) having the following composition:
- 5.0 percent of pulverized whole soybean
- 1.5 percent of yeast
- 0.15 percent of $K_2HPO_4$
- 0.5 percent of soybean oil
- 0.1 percent of $MgSO_4.7H_2O$
- 0.1 percent of silicone oil (sold from Shin-etsu Chemical Industry Co., Ltd. under trademark "KM-70")
- 2.0 percent of cholesterol
- 1.0 percent of dry egg yolk, and
- remainder-water.

The flasks and their contents are sterilized by autoclaving for a period of 20 minutes at a temperature of 120° C. Each of the flask is inoculated with 2 ml of the seed culture broth obtained above. The main fermentation is initiated at a temperature of 30° C. on a reciprocal shaker having a 7-cm stroke at 120 strokes per minute. The incubation of the first and second groups is stopped at the end of 140 hours and 210 hours, respectively, from the time of initiating the incubation. The combined fermentation broth of each group is extracted twice each with 1 l of ethyl acetate.

After the combined extract is filtered to remove any insoluble such as cell, the steroid content of the filtrate is determined by gas-chromatographic analysis. The analysis shows that the extracts of the first and second groups contain 1.65 g and 1.85 g, respectively, of the formed 9α-OH-4AD.

The above-mentioned procedure is repeated with the same main fermentation medium except that no egg yolk is added. The incubation of the first and second groups (each group consisting of ten flasks, i.e., a total of twenty flasks are used) is stopped at the end of 140 hours and 210 hours, respectively, from the start of incubation and the fermentation broth is extracted in the same way. Analysis of the extracts with respect to steroid content shows that the extracts of the first and second groups contain 0.94 g and 1.38 g, respectively, of 9α-OH-4AD.

EXAMPLE 2

A seed medium (pH 7.2) having the following composition is prepared:
- 1.0 percent of glucose
- 1.0 percent of meat extract
- 1.0 percent of peptone, and
- remainder-water.

To a 500 ml shaker flask is added 100 ml of the seed medium. The flask and its contents are sterilized by autoclaving for a period of 15 minutes at a temperature of 120° C. The medium is inoculated with a loopful of *M. vaccae* MCI-1104 and the inoculated medium is incubated for a period of 48 hours at a temperature of 30° C. on a reciprocal shaker having a 7-cm stroke at 120 strokes per minute.

Each of two (2) 500 ml shaker flasks each containing 50 ml of a main fermentation medium (pH 7.0, sterilized by autoclaving for 20 minutes at 120° C.) having the following composition:
- 4.0 percent of pulverized defatted soybean
- 2.0 percent of yeast
- 1.0 percent of soybean oil
- 1.0 percent of rice bran
- 0.2 percent of $NaNO_3$
- 0.1 percent of $K_2HPO_4$
- 0.1 percent of $MgSO_4.7H_2O$
- 1.5 percent of cholesterol
- 0.5 percent of dry egg yolk, and
- remainder-water is inoculated with 20 ml of the seed culture broth prepared above. The main fermentation is conducted at 30° C. on a reciprocal shaker having a 7-cm stroke at 100 strokes per minute. The fermentation is continued for 144 hours in one flask and for 192 hours in the other flask. Each fermentation broth is extracted twice each with 100 ml of ethyl acetate. Analysis of the extracts shows that these extracts contain 95 mg and 115 mg, respectively, of 9α-OH-4AD. The above-mentioned procedure is repeated with the same main fermentation medium except that no egg yolk is added. Similarly the fermentation in the two flasks is stopped 144 hours and 192 hours, respectively, after the start of main fermentation. Analysis of the extracts with respect to steroid content shows that they contain 52 mg and 98 mg, respectively, of 9α-OH-4AD.

EXAMPLE 3

The procedure described in Example 2 is repeated except that crude β-sitosterol (a 8:1:1 mixture of β-sitosterol, campesterol and α-sitosterol), a 2:1 mixture of β-sitosterol and campesterol, stigmasterol, cholest-4-en-3-one, cholesteryl oleate or 4BN is used as the substrate in place of cholesterol and that the main fermentation is continued for 140 hours. The amounts of 9α-OH-4AD built up in the broth are shown in Table 2.

TABLE 2

| Sterol | 9α-OH—4AD (mg) Addition of egg yolk | |
|---|---|---|
| | Yes | No |
| Crude β-sitosterol | 57 | 38 |
| β-Sitosterol + campesterol | 62 | 39 |
| Stigmasterol | 10 | 7 |
| Cholest-4-en-3-one | 43 | 22 |
| Cholesteryl oleate | 5 | 4 |
| 4BN | 12 | 6 |

EXAMPLE 4

A seed medium (pH 7.2) having the following composition is prepared:
- 1.0 percent of glucose
- 1.0 percent of meat extract
- 1.0 percent of peptone, and
- remainder-water.

To a 500 ml shaker flask is added 100 ml of the seed medium. The flask and its contents are sterilized by autoclaving for a period of 15 minutes at a temperature of 120° C. The medium is inoculated with a loopful of *M. parafortuitum* complex MCI 0801 and the inoculated medium is incubated for a period of 48 hours at a temperature of 30° C. on a reciprocal shaker having a 7-cm stroke at 120 strokes per minute.

Each of ten (10) 500 ml shaker flasks each containing 50 ml of a main fermentation medium (pH 7.0, sterilized by autoclaving at 120° C. for 20 minutes) having the composition:

4.0 percent of pulverized whole soybean
0.2 percent of NaNO$_3$
0.2 percent of K$_2$HPO$_4$
0.1 percent of MgSO$_4$.7H$_2$O
1.0 percent of cholesterol, and
remainder-water is inoculated with 2 ml of the seed culture broth prepared above. Each of another ten (10) 500 ml shaker flask each containing 50 ml of a main fermentation medium (pH 7.0, sterilized in the same way) having the same composition as above except that it further contains 1.0 percent of dry egg yolk is inoculated with 2 ml of the same seed culture broth. The main fermentation is initiated at 30° C. on a reciprocal shaker having a 7-cm stroke at 120 strokes per minute and stopped after 112 hours in five (5) flasks and after 170 hours in the other five flasks. The combined fermentation broths in the first five flasks and in the second five flasks are each extracted with two 1-liter portions of ethyl acetate.

After filtration of the extract to remove any insoluble, the ADD content of the filtrate is determined by gas chromatography. The results are shown in Table 3.

TABLE 3

| Addition of egg yolk | Amount of ADD formed (g) | |
|---|---|---|
| | Incubation time (hr.) | |
| | 112 | 170 |
| No | 0.16 | 0.48 |
| Yes | 0.47 | 0.61 |

EXAMPLE 5

A seed medium (pH 7.2) having the following composition is prepared:

1.0 percent of glucose
1.0 percent of meat extract
1.0 percent of peptone, and
remainder-water.

To a 500 ml shaker flask is added 100 ml of the seed medium. The flask and its contents are sterilized by autoclaving for a period of 15 minutes at a temperature of 120° C. The medium is inoculated with a loopful of *M. parafortuitum* complex MCI 0802 and the inoculated medium is incubated for a period of 48 hours at a temperature of 30° C. on a reciprocal shaker having a 7-cm stroke at 120 strokes per minute.

With 20 ml of the seed culture broth are inoculated each of two (2) 6 l shaker flasks each containing 800 ml of a main fermentation medium (pH 7.0, sterilized by autoclaving at 120° C. for 20 minutes) having the following composition:

2.0 percent of pulverized whole soybean
2.0 percent of yeast
4.0 percent of glycerol
0.2 percent of NaNO$_3$
0.2 percent of K$_2$HPO$_4$
0.1 percent of MgSO$_4$.7H$_2$O
1.5 percent of cholesterol, and
remainder-water, and each of two (2) 6 l shaker flasks each containing 800 ml of a main fermentation medium (pH 7.0, sterilized in the same way) having the same composition as above except for addition of 1.5 percent of dry egg yolk. The main fermentation in each group is initiated at 30° C. on a reciprocal shaker having a 7-cm stroke at 100 strokes per minute, and continued for 130 hours in one flask and for 180 hours in the other flask. Each fermentation broth thus obtained is extracted with 2.4 l of ethyl acetate.

The ADD contents of the extracts are determined gas chromatographically. The results are shown in Table 4.

TABLE 4

| Addition of egg yolk | Amount of ADD formed (g) | |
|---|---|---|
| | Incubation time (hr.) | |
| | 130 | 180 |
| No | 1.65 | 2.65 |
| Yes | 2.65 | 3.27 |

EXAMPLE 6

A seed medium (pH 7.2) having the following composition is prepared:

1.0 percent of glucose
1.0 percent of meat extract
1.0 percent of peptone, and
remainder-water.

To a 500 ml shaker flask is added 100 ml of the seed medium. The flask and its contents are sterilized by autoclaving for a period of 15 minutes at a temperature of 120° C. The medium is inoculated with a loopful of *M. parafortuitum* complex MCI 0807 and the inoculated medium is incubated for a period of 48 hours at a temperature of 30° C. on a reciprocal shaker having a 7-cm stroke at 120 strokes per minute.

With 2 ml of the seed culture broth is inoculated a 500 ml shaker flask containing 100 ml of a main fermentation medium (pH 7.0, sterilized by autoclaving at 120° C. for 20 minutes) having the composition:

4.0 percent of pulverized whole soybean
0.2 percent of NaNO$_3$
0.2 percent of K$_2$HPO$_4$
0.1 percent of MgSO$_4$.7H$_2$O
2.0 percent of cholesterol
various percent of egg yolk, and
remainder-water.

The main fermentation is continued at 30° C. for 110 hours on a reciprocal shaker having a 7-cm stroke at 120 strokes per minute, and the resulting fermentation broth is extracted twice each with 200 ml of ethyl acetate.

The combined extract is filtered to remove any insoluble matter such as cell, and the filtrate is assayed for 4AD by gas chromatography. The results are shown in Table 5.

TABLE 5

| % Dry egg yolk | 4AD formed (g) |
|---|---|
| 0 | 0.20 |
| 0.1 | 0.29 |
| 0.2 | 0.31 |
| 0.3 | 0.39 |

TABLE 5-continued

| % Dry egg yolk | 4AD formed (g) |
|---|---|
| 0.5 | 0.45 |
| 0.7 | 0.50 |
| 1.0 | 0.50 |
| 1.5 | 0.48 |
| 2.0 | 0.42 |
| 3.0 | 0.40 |
| 4.0 | 0.30 |
| 7.0 | 0.25 |

EXAMPLE 7

A seed medium (pH 7.2) having the following composition is prepared:
1.0 percent of glucose
1.0 percent of meat extract
1.0 percent of peptone, and
remainder-water.

To a 500 ml shaker flask is added 100 ml of the seed medium. The flask and its contents are sterilized by autoclaving for a period of 15 minutes at a temperature of 120° C. The medium is inoculated with a loopful of M. parafortuitum complex MCI 0807 and the inoculated medium is incubated for a period of 48 hours at a temperature of 30° C. on a reciprocal shaker having a 7-cm stroke at 120 strokes per minute.

With 20 ml of the seed culture broth is inoculated each of two (2) 6 l shaker flasks each containing 800 ml of a main fermentation medium (pH 7.0, sterilized by autoclaving at 120° C. for 20 minutes) having the following composition.
2.0 percent of pulverized defatted soybean
2.0 percent of yeast
1.0 percent of dry egg yolk
0.2 percent of NaNO$_3$
0.2 percent of K$_2$HPO$_4$
0.1 percent of MgSO$_4$.7H$_2$O
2.0 percent of cholesterol, and
remainder-water.

The fermentation medium in one flask contains no egg yolk. The main fermentation is conducted at 30° C. on a reciprocal shaker having a 7-cm stroke at 100 strokes per minute. During the fermentation, 20 ml samples are withdrawn at intervals and each sample is extracted with 60 ml of ethyl acetate and assayed. The 4AD content of the extract is shown in Table 6.

TABLE 6

| Incubation time (hr.) | 4AD (mg) Addition of egg yolk | |
|---|---|---|
| | No | Yes |
| 48 | 7 | 27 |
| 72 | 20 | 57 |
| 96 | 37 | 82 |
| 120 | 52 | 100 |
| 144 | 77 | 105 |
| 168 | 90 | 105 |
| 192 | 95 | 100 |

EXAMPLE 8

The procedure described in Example 6 is repeated except that the dry egg yolk is replaced by raw egg yolk. The results are shown in Table 7.

TABLE 7

| % raw egg yolk | 4AD formed (g) |
|---|---|
| 0 | 0.20 |
| 0.2 | 0.30 |
| 0.5 | 0.39 |
| 1.0 | 0.44 |
| 2.0 | 0.50 |
| 4.0 | 0.41 |
| 8.0 | 0.27 |

EXAMPLE 9

The procedure described in Example 6 is repeated except that the dry egg yolk is replaced by whole egg (from which the shell is removed). The results are shown in Table 8.

TABLE 8

| % whole egg | 4AD formed (g) |
|---|---|
| 0 | 0.20 |
| 0.5 | 0.29 |
| 1.0 | 0.35 |
| 1.5 | 0.40 |
| 3.0 | 0.47 |
| 5.0 | 0.50 |
| 10.0 | 0.38 |

EXAMPLE 10

A seed medium (pH 7.2) having the following composition is prepared:
1.0 percent of glucose
1.0 percent of meat extract
1.0 percent of peptone, and
remainder-water.

To a 500 ml shaker flask is added 100 ml of the seed medium. The flask and its contents are sterilized by autoclaving for a period of 15 minutes at a temperature of 120° C. The medium is inoculated with a loopful of M. fortuitum NRRL B-8119 and the inoculated medium is incubated for a period of 48 hours at a temperature of 30° C. on a reciprocal shaker having a 7-cm stroke at 120 strokes per minute.

With 20 ml of the seed culture broth are inoculated each of two (2) 6 l shaker flasks each containing 800 ml of a main fermentation medium (pH 7.0, sterilized by autoclaving at 120° C. for 20 minutes) having the following composition:
4.0 percent of pulverized whole soybean
0.8 percent of soybean oil
0.2 percent of NaNO$_3$
0.2 percent of K$_2$HPO$_4$
0.1 percent of MgSO$_4$.7H$_2$O
1.5 percent of cholesterol, and
remainder-water,
and each of two (2) 6 l shaker flasks each containing 800 ml of a main fermentation medium (pH 7.0, sterilized in the same way) having the same composition as above except for addition of 1.0 percent of dry egg yolk. The main fermentation in each group is initiated at 30° C. on a reciprocal shaker having a 7-cm stroke at 100 strokes per minute, and continued for 120 hours in one flask and for 168 hours in the other flask. Each fermentation broth thus obtained is extracted with 2.4 l of ethyl acetate.

The 9α-OH-4AD contents of the extracts are determined gas chromatographically. The results are shown in Table 9.

TABLE 9

| Addition of egg yolk | Amount of 9α-OH—4AD formed (g) | |
|---|---|---|
| | Incubation time (hr.) | |
| | 120 | 168 |
| No | 1.75 | 2.77 |
| Yes | 2.88 | 3.28 |

EXAMPLE 11

The procedure described in Example 10 is repeated except that *M. fortuitum* NRRL B-8119 is replaced by M. sp. NRRL B-3683. The ADD contents of the extracts are shown in Table 10.

TABLE 10

| Addition of egg yolk | Amount of ADD formed (g) | |
|---|---|---|
| | Incubation time (hr.) | |
| | 120 | 168 |
| No | 2.01 | 3.12 |
| Yes | 2.64 | 3.25 |

EXAMPLE 12

The procedure described in Example 10 is repeated except that *M. fortuitum* NRRL B-8119 is replaced by M. sp. NRRL B-3805. The 4AD contents of the extracts are shown in Table 11.

TABLE 11

| Addition of egg yolk | Amount of 4AD formed (g) | |
|---|---|---|
| | Incubation time (hr.) | |
| | 120 | 168 |
| No | 1.68 | 3.85 |
| Yes | 3.51 | 4.10 |

Having now fully described the invention, it will be apparent to one of ordinary skill in the art that many changes and modifications can be made thereto without departing from the spirit or scope of the invention as set forth herein.

What is claimed as new and intended to be covered by Letters Patents:

1. A process for producing an androstane steroid which comprises converting a sterol substrate with a microorganism of the genus Mycobacterium using a culture medium containing at least 0.1% by weight of dry egg yolk.

2. The process of claim 1 wherein the androstane steroid is selected from the group consisting of androst-4-ene-3,17-dione, androsta-1,4-diene-3,17-dione and 9α-hydroxyandrost-4-ene-3,17-dione.

3. The process of claim 1 or 2 wherein the sterol substrate is selected from the group consisting of sterols, their C-3 ester derivatives, their C-3 ether derivatives and the intermediates formed during the oxidation thereof.

4. The process of any of claims 1 to 3 wherein the microorganism is a mutant which is lacking in or weak in the enzymes degrading the androstane steroid.

5. The process of claim 4 wherein the microorganism is a mutant belonging to *Mycobacterium parafortuitum* complex.

6. The process of claim 4 wherein the microorganism is a mutant belonging to *Mycobacterium vaccae*.

7. The process of claim 5 wherein the microorganism is selected from the group consisting of *Mycobacterium parafortuitum* complex MCI 0801 and MCI 0802 and the androstane steroid is androsta-1,4-diene-3,17-dione.

8. The process of claim 5 wherein the microorganism is *Mycobacterium parafortuitum* complex MCI 0807 and the androstane steroid is androst-4-ene-3,17-dione.

9. The process of claim 4 or claim 6 wherein the microorganism is selected from the group consisting of *Mycobacterium vaccae* MCI 1104 and MCI 1117 and the androstane steroid is 9α-hydroxyandrost-4-ene-3,17-dione.

10. The process of claim 4 wherein the microorganism is Mycobacterium sp. NRRL B-3683 and the androstane steroid is androsta-1,4-diene-3,17-dione.

11. The process of claim 4 wherein the microorganism is Mycobacterium sp. NRRL B-3805 and the androstane steroid is androst-4-ene-3,17-dione.

* * * * *